United States Patent

Battistini et al.

[11] 4,337,248
[45] Jun. 29, 1982

[54] PAROMOMYCIN CONTAINING COMPOUNDS AND METHOD OF USE

[75] Inventors: Carlo Battistini, Novate Milanese; Giuseppe Cassinelli, Voghera; Giovanni Franceschi; Rosanna Mazzoleni, both of Milan; Federico Arcamone, Nerviano, all of Italy

[73] Assignee: Farmitalia Carlo Erba S.p.A., Milan, Italy

[21] Appl. No.: 156,478

[22] Filed: Jun. 4, 1980

[30] Foreign Application Priority Data

Jun. 7, 1979 [GB] United Kingdom ............... 7919778

[51] Int. Cl.³ .................. A61K 31/71; C07H 15/22
[52] U.S. Cl. ............................ 424/180; 424/181; 536/13.3
[58] Field of Search ............. 424/180; 536/12, 17 R

[56] References Cited

U.S. PATENT DOCUMENTS

| | | | |
|---|---|---|---|
| 3,920,628 | 11/1975 | Daniels | 536/17 |
| 4,029,883 | 6/1977 | Hiraga et al. | 536/17 |
| 4,051,315 | 9/1977 | Godfrey et al. | 536/17 |
| 4,078,138 | 3/1978 | Akita et al. | 536/17 |
| 4,247,687 | 1/1981 | Hanessian | 536/17 |

Primary Examiner—Johnnie R. Brown
Attorney, Agent, or Firm—Stevens, Davis, Miller & Mosher

[57] ABSTRACT

Compounds are disclosed of the formula

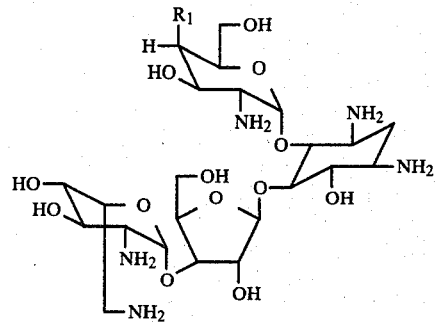

wherein $R_1$ represents a hydrogen or chlorine atom, as well as intermediates. These include 4'-deoxy-paromomycin; 4'-deoxy-4'-epi-chloro-paromomycin; 4'-deoxy-4'-epi-chloro-penta-N-benzyloxycarbonylparomomycin; 4'-deoxy-penta-N-benzyloxycarbonylparomomycin; 6,3',2'',5'',3''',4'''-hexa-O-acetyl-6'-O-benzoyl-4'-deoxy-penta-N-benzyloxycarbonylparomomycin; 6,3',2'',5'',3''',4'''-hexa-O-acetyl-6'-O-benzoyl-4'-epi-chloro-4'-deoxy-penta-N-benzyloxycarbonylparomomycin; 6,3',2'',5'',3''',4'''-hexa-O-acetyl-6'-O-benzyl-penta-N-benzyloxycarbonylparomomycin; 6,3',2'',5'',3''',4'''-hexa-O-acetyl-6'-O-benzoyl-4'-O-[(methylthio)-thiocarbonyl]-penta-N-benzyloxycarbonylparomomycin; and 6,3',2'',5'',3''',4'''-hexa-O-acetyl-6'-O-benzoyl-4'-O-[(phenylthio)-thiocarbonyl]-penta-N-benzyloxycarbonylparomomycin. The compounds illustrated by the structural formula are useful in treating amoebic dysentery in man and animals.

17 Claims, No Drawings

PAROMOMYCIN CONTAINING COMPOUNDS AND METHOD OF USE

This invention relates to paromomycin derivatives, their preparation, and therapeutic compositions containing them.

The invention provides novel compounds represented by the general formula

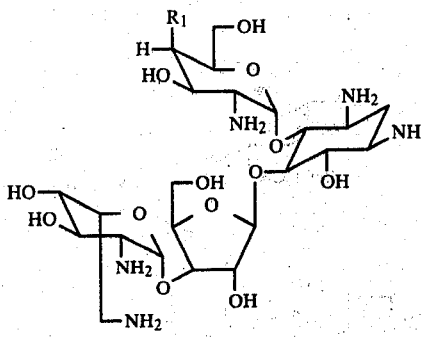

wherein $R_1$ represents a hydrogen or chlorine atom.

The process according to the invention is illustrated with regard to permissible variants thereof by the following reaction scheme, in which A represents an acyl or benzoyl group, Ph represents a phenyl group, and Bn represents a benzyl group:

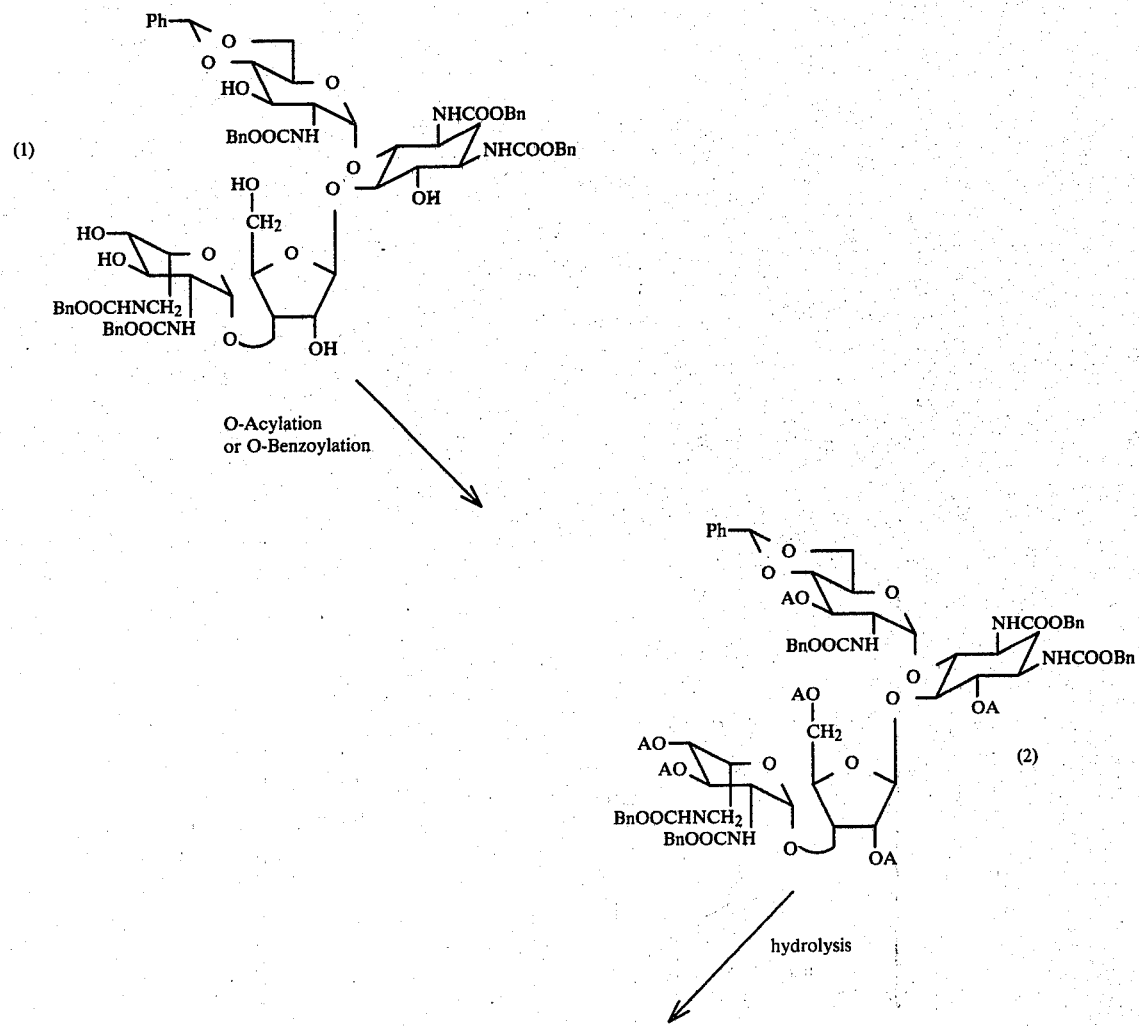

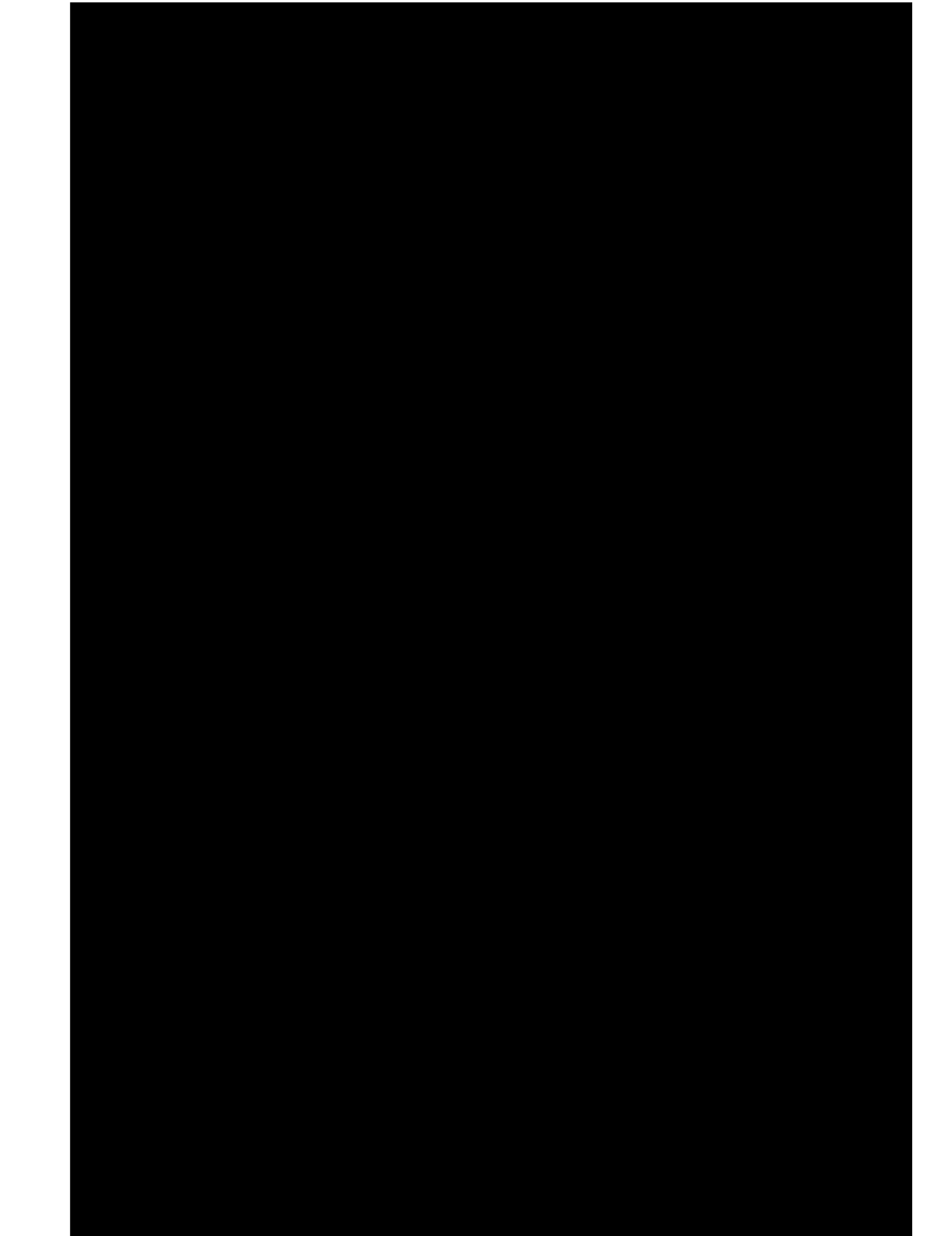

-continued
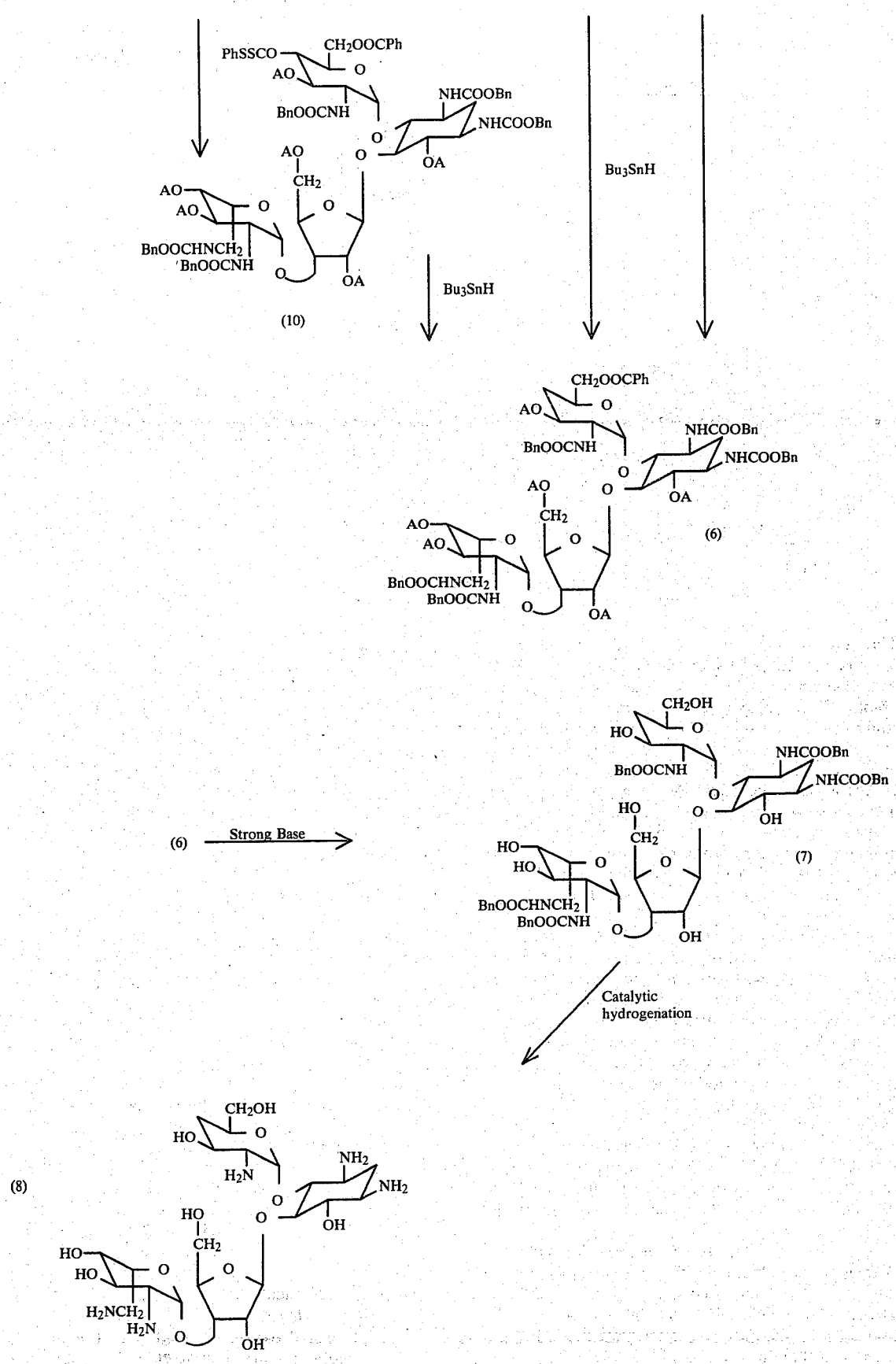

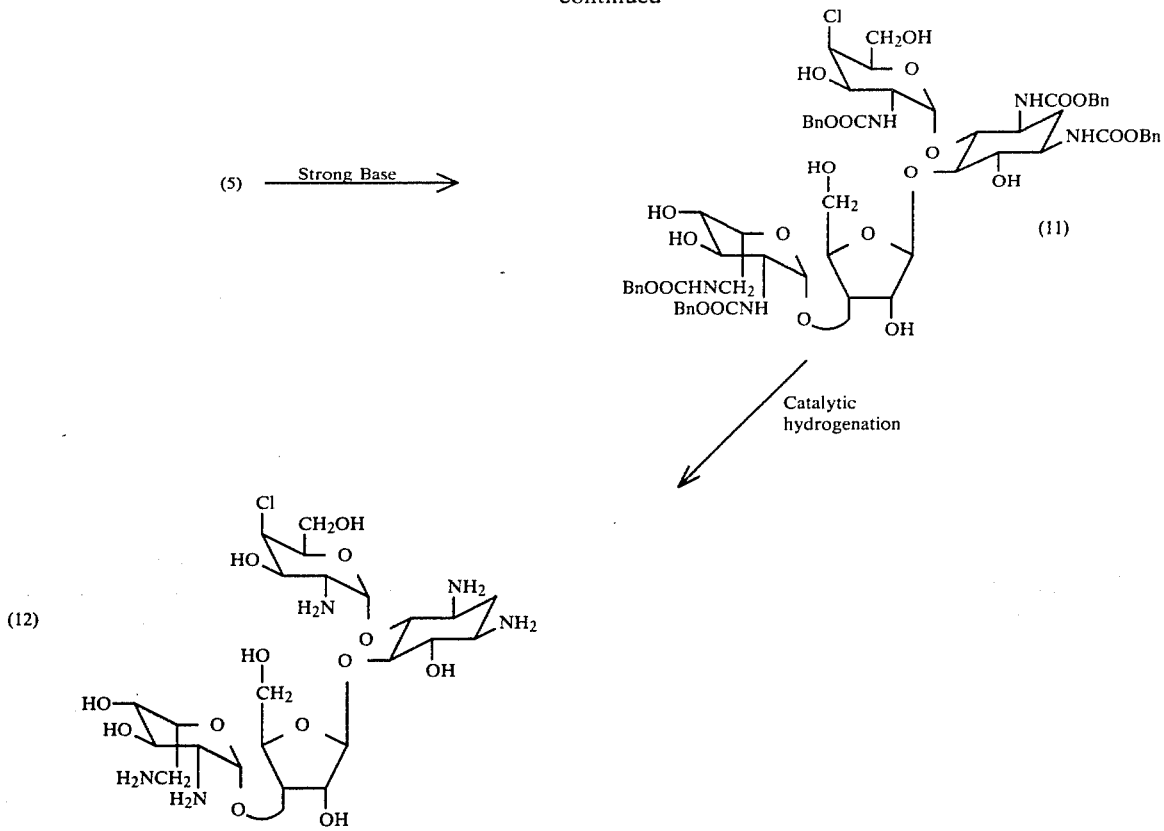

The starting material, 4',6'-O-benzylidene-penta-N-benzyloxycarbonylparomomycin (1), may be prepared from paromomycin which is a natural aminoglycoside antibiotic (U.S. Pat. Nos. 2,916,485 and 3,065,147), according to the procedures described by S. Hanessian et al. in Tetrahedron Letters 4009 (1974) and in Canad. J. Chem., 56, 1482 (1978).

O-Acylation or benzoylation gives the hexa-O-acyl or hexa-O-benzoyl derivative (2) which, by hydrolysis of the O-benzylidene group, gives the compound (3) containing two free hydroxy groups at C-4' and C-6'. Selective benzoylation at the 6'-position yields the 6'-O-benzoyl derivative (4), a key intermediate having a single free hydroxy group at the 4'-position.

Three alternative routes are available from compound (4) to compound (6). The first is chlorination of the compound (4) with sulphuryl chloride in the presence of a base, preferably pyridine, to give the 4'-epi-chloro-4'-deoxy derivative (5) and dechlorination by treatment with tributyltin hydride, suitably in toluene in the presence of azobisisobutyronitrile.

The second route is via the S-methyl dithiocarbonate (9), prepared by reacting compound (4) with carbon disulphide, a strong base, and methyl iodide following the procedure described by T. Hayashi et al., Chem. Pharm. Bull., 26, 1986 (1978). The strong base is preferably sodium hydroxide. The S-methyl dithiocarbonate may then be reduced with tributyltin hydride to give the compound (6).

The third route is via the S-phenyl dithiocarbonate (10). This may be obtained from compound (4) by treatment with phenylthio-thiocarbonyl chloride, $C_6H_5S.CS.Cl$, in the presence of a base, preferably pyridine, following the procedure described by T. Hayashi et al., Chem. Pharm. Bull., 26, 1786 (1978). The S-phenyl dithiocarbonate (10) may be reduced with tributyltin hydride in the same way as the S-methyl dithiocarbonate (9) to give the compound (6).

De-O-acylation or de-O-benzoylation of compound (6) gives 4'-deoxy-penta-N-benzyloxycarbonylparomomycin (7), which may be reduced by catalytic hydrogenolysis in the presence of 10% palladium-on-charcoal to give 4'-deoxyparomomycin (8). This may be purified by ion exchange on a column.

Similar de-O-acylation or de-O-benzoylation of compound (5) instead of compound (6) and similar reduction of the resultant compound (11) gives 4'-deoxy-4'-epi-chloroparomomycin (12).

Compounds of formula (5), (6), (7), (9), (10), (11) are new compounds and are within the scope of the present invention.

4'-deoxyparomomycin (8) and 4'-deoxy-4'-epi-chloroparomomycin (12) are useful as antibacterial agents, active against gram-positive and gram-negative bacteria and against protozoa.

The most straightforward approach to improving the spectrum of antibacterial activity of natural aminoglycoside antibiotics has been to remove or sterically hinder sites of enzymatic inactivation. It is known that the hydroxy group at 3'-position in the aminoglycoside antibiotics is susceptible of enzymatic inactivation by phosphotransferase enzymes produced by resistant bacterial strains and also that the absence of this group leads to enhanced activity (Kirk-Othmer: "Encyclopeidia of Chemical Technology", Vol. 2, 3rd Ed. 1978 by John Wiley & Sons, Inc.). Since the adjacent C-4' bearing a hydroxy group might be intimately involved in binding the inactivating enzymes, any modifications such as introduction of a chlorine atom or removal of the hydroxy group might be expected to lead to weaker binding and aberrant recognition.

The invention further provides a pharmaceutical composition comprising 4'-deoxyparomomycin (8) or 4'-deoxy-4'-epi-chloroparomomycin (12) in admixture with a pharmaceutically acceptable diluent or carrier.

Biological Activity

4'-deoxy-paromomycin (8) and 4'-deoxy-4'-epi-chloroparomomycin (12) display antibacterial activity "in vitro".

The "in vitro" tests are carried out with the method of serial dilutions in liquid medium (Nutrient Broth Difco) and the minimal inhibition concentration (MIC) is determined after 24 hours incubation at 37° C.

As indicated in the Table below, 4'-deoxy-paromomycin (8) shows similar potency when compared with paromomycin, against sensitive strains and an increased activity against some resistant strains of gram-negative bacteria.

TABLE

The minimum inhibitory concentrations (Mcg/ml) of compounds (8) and (12) in comparison with paromomycin

| Strain | Inactivating enzyme* | paromomycin | (8) | (12) |
|---|---|---|---|---|
| Staphylococcus aureus 209P | | 1.55 | 1.55 | 6.25 |
| Escherichia coli K 12 | | 12.5 | 12.5 | 50 |
| Escherichia coli K 12-R 112 | APH (3') I | >200 | >200 | >200 |
| Escherichia coli K 12-R 148 | APH (3') II | >200 | 50 | 200 |
| Escherichia coli K 12-R 55 | AAC (3) I | 6.25 | 6.25 | 50 |

*APH (3') I: aminoglycoside 3'-phosphotransferase I
APH (3') II: aminoglycoside 3'-phosphotransferase II
AAC (3) I: aminoglycoside 3-acetyltransferase I The novel compounds may be used as antibiotics to treat similar diseases in a similar way to the parent compound paryomomycin, the dosage being similar to those of paromomycin.

The usual solvents, diluents and carriers of a pharmaceutically accceptable nature may be used in the preparation of suitable doses. The paromomycin derivatives are useful for the treatment of amoebic disentery, shigellosis, and salmonellosis.

Thus, the compounds of this invention are valuable as anti-bacterial agents (especially for the suppression of intestinal bacteria), nutritional supplements in animal feeds, therapeutic agents in poultry and animals, including man, and are especially valuable in the treatment of infectious diseases caused by Gram-positive and Gram-negative bacteria. They may be used in the treatment of systemic bacterial infections when administered parenterally in the dosage range of about 250 mg to about 3000 mg per day in divided doses three or four times a day. Generally the compounds are effective when administered at a dosage of about 5.0 to 7.5 mg/kg of body weight every 12 hours.

In addition to the compounds themselves, pharmaceutically acceptable salts thereof can be formed and used in the usual way. For example, the mono-, di-, tri-, tetra- or penta-salts (where appropriate) can be formed by the interreaction of one mole of the stated compounds with 1 to 5 moles of a pharmaceutically acceptable acid, e.g. citric acid, ascorbic acid, acetic acid, hydrochloric acid, sulfuric acid, maleic acid, nitric acid, phosphoric acid, hydrobromic acid, and other acids commonly used to form the salts of basic pharmaceuticals.

The following Examples, in which all temperatures are in degrees Centigrade, still further illustrate the invention.

EXAMPLE 1

Hexa-O-acetyl-4',6'-O-benzylidene-penta-N-benzyloxycarbonylparomomycin (2; A=acetyl)

11.1 g of 4',6'-O-benzylidene-penta-N-benzyloxycarbonylparomomycin (1) (prepared as described in Can. J. Chem., 56, 1482 1978) were dissolved in 112 ml of pyridine and 56 ml of acetic anhydride were added. After three days at room temperature, the solution was added slowly to stirred ice and water. After stirring for 1 hour, the white solid obtained was filtered off, copiously washed with water, and dissolved in methanol. Evaporation off of the solvent gave 12.7 g of the title compound.

M.p. 124°–127°.

$[\alpha]_D^{25} + 21.0$ (c 0.500 CHCl$_3$).

N.M.R. spectrum (60 MHz, CDCl$_3$) showed the correct aromatic/acetyl proton ratio (1.66).

EXAMPLE 2

6,3',2'',5'',3''',4'''-Hexa-O-acetyl-penta-N-benzyloxycarbonyl-paromomycin (3; A=acetyl)

A solution containing 12.3 g of the compound prepared in the preceding Example in 500 ml of acetic acid and 125 ml of water was allowed to stand for 90 hours at room temperature. The solvent was then evaporated off and the residue was dissolved in methanol and evaporated to dryness several times to give 11.6 g of the title compound as an amorphous solid.

M.p. 116°–119°.

$[\alpha]_D^{25} + 19.9$ (c 0.537 CHCl$_3$).

N.M.R. spectrum (60 MHz, CDCl$_3$) showed the correct aromatic/acetyl proton ratio (1.38).

EXAMPLE 3

6,3',2'',5'',3''',4'''-Hexa-O-acetyl-6'-O-benzoyl-penta-N-benzyloxy-carbonylparomomycin (4; A=acetyl)

10.1 g of the compound prepared in Example 2 were dissolved in 100 ml of dry pyridine and the solution was cooled to 0°. A solution of 0.84 ml of benzoyl chloride in 2 ml of pyridine was added slowly and with stirring. The reaction mixture was kept at 0° and monitored by TLC. After 43 hours, 0.42 ml of benzoyl chloride in 1 ml of pyridine was added. After 67 hours more reagent was added (0.2 ml of benzoyl chloride in 0.5 ml of pyridine) and, after a total period of 96 hours, water was added and the mixture extracted with chloroform. The extracts were washed with water, 2 M hydrochloric acid, water, aqueous sodium bicarbonate, and water in that order. After drying and evaporation, 10.9 g of residue was obtained. The crude product was chromatographed on silica gel (0–2% methanol in chloroform) to give 5.8 g of the title compound in pure form.

M.p. 110°–115°; $[\alpha]_D^{25} + 26.3$ (c 1.096 CHCl$_3$)

Analysis:

Calcd. for $C_{82}H_{91}N_5O_{31}$: C 59.95, H 5.58, N 4.26.
Found: C 59.87, H 5.77, N 4.19.

N.M.R. spectrum (60 MHz, CDCl$_3$) showed the correct aromatic/acetyl proton ratio (1.67).

EXAMPLE 4

6,3',2",5",3'",4'"-Hexa-O-acetyl-6'-O-benzoyl-4'-epichloro-4'-deoxy-penta-N-benzyloxycarbonylparomomycin (5; A=acetyl)

1 g of the compound prepared in Example 3 was dissolved in 15 ml of dry pyridine and 1.3 ml of sulfuryl chloride were added dropwise to the cooled (0°) solution. After stirring for 3 hours at 0° and 18 hours at room temperature, most of the solvent was eliminated under vacuum and chloroform and water were added. After extraction with chloroform, extracts were washed with water, dried and evaporated 'in vacuo'. The crude product was purified by preparative TLC and reprecipitation from chloroform-ether-hexane, to give 515 mg of the title compound in pure form. The compound showed the presence of chlorine and had Rf 0.37 in the solvent system toluene:ethyl acetate (1:1 by volume) (starting product 4:Rf 0.23).

M.p. 105°–115°; $[\alpha]_D^{25}$ +30.3 (c 1.012 CHCl$_3$)

Analysis: Calcd. for $C_{82}H_{90}ClN_5O_{30}$: C 59.29, H 5.46, Cl 2.13, N 4.21. Found: C 58.38, H 5.41, Cl 2.36, N. 4.14.

EXAMPLE 5

6,3',2",5",3'",4'"-Hexa-O-acetyl-6'-O-benzoyl-4'-deoxy-penta-N-benzyloxycarbonylparomomycin (6; A=acetyl)

A solution containing 400 mg of the compound prepared in Example 4 in 16 ml of toluene was heated to reflux under a nitrogen atmosphere and 0.8 ml of tributyltin hydride in 0.8 ml of toluene and 20 mg of azobisisobutyronitrile were added. After 3 hours under reflux, the solvent was evaporated off and the solid residue was washed with n-hexane, dissolved in chloroform, and added to a mixture of diethyl ether and n-hexane to precipitate 385 mg of the title compound in a form sufficiently pure for subsequent reactions. In the solvent system toluene:ethyl acetate (1:1 by volume), the compound had an RF of 0.31.

M.p. 125°–130°; $[\alpha]_D^{25}$ +33.0 (c 1.116 CHCl$_3$)

Analysis: Calcd. for $C_{82}H_{91}N_5O_{30}$: C 60.54, H 5.63, N 4.30. Found: C 59.90, H 5.59, N 4.30.

EXAMPLE 6

4'-Deoxy-penta-N-benzyloxycarbonylparomomycin (7)

385 mg of the compound prepared in Example 5, without further purification, were dissolved in 14 ml of 0.05 N methanolic sodium methoxide and stirred at room temperature for 3 hours. Solid carbon dioxide and water were added and the solution was evaporated to dryness. Water was added to the residue and the mixture was extracted several times with ethyl acetate. The combined organic extracts were washed with water and evaporated to dryness to give 205 mg of crude product. Purification by preparative TLC, using chloroform:ethyl acetate:methanol (40:25:9 by volume) as eluant, yielded 130 mg of the title compound in pure form, having an Rf of 0.22 in the same solvent system.

M.p. 125°–130°; $[\alpha]_D^{25}$ +41.0 (c 0.900 CHCl$_3$)

Analysis: Calcd. for $C_{63}H_{75}N_5O_{23}$: C 59.56, H 5.95, N 5.51.

Found: C 58.74, H 5.78, N 5.36.

EXAMPLE 7

4'-Deoxy paromomycin (8)

To a solution of 130 mg of the compound prepared in Example 6 in 16 ml of 80% ethanol, 1 ml of cyclohexene and 200 mg of 10% palladium-on-carbon were added. The mixture was refluxed for 1½ hours, filtered and evaporated 'in vacuo' to give 50 mg of residue. The crude product was purified on a column of CG 50 ($NH_4^+$ form, 100–200 mesh) yielding 21 mg of the title compound in pure form, m.p. 175°–180° with decomposition.

The product was homogeneous on TLC in the solvent system 28% ammonia:butanol:ethanol:water (5:8:10:7 by volume) and had an Rf (double development) of 0.33, slightly higher than the Rf of lividomycin B (3'-deoxy-paromomycin):0.30.

Mass spectrum (field desorption) showed a peak at m/e 600 (MH+), and fragments at 440 and 455 indicating the deoxygenation site to be in ring A.

The product (free base) was converted into the sulphate form by adding 0.2 M sulphuric acid at pH 6.4.

M.p. (dec.) 230° (sulphate form)

$[\alpha]_D^{25}$ +58 (c 1.115 H$_2$O) (sulphate form)

Analysis (sulphate form): Calcd. for $C_{23}H_{45}N_5O_{13}$·5/2 H$_2$SO$_4$: C 32.70, H 5.96, N 8.29. Found: C 33.51, H 6.47, N 7.83.

$^{13}$C NMR (D$_2$O) (free base): 100.2 (C 1'), 57.2 (C 2'), 68.8 (C 3'), 34.7 (C 4'), 67.9 (C 5'), 64.0 (C 6').

EXAMPLE 8

6,3',2",5",3'",4'"-Hexa-O-acetyl-6'-O-benzoyl-4'-O-[(methylthio)thiocarbonyl]-penta-N-benzyloxycarbonylparomomycin (9; A=acetyl)

5 N sodium hydroxide (0.28 ml) was added dropwise to an ice-cold solution of 400 mg of the compound prepared in Example 3 and 0.4 ml of carbon disulphide in 3 ml of dimethylsulphoxide. The mixture was stirred for 20 minutes at 0°. Then 0.6 ml of methyl iodide were added with cooling and the mixture was stirred at room temperature for 30 minutes. Excess of volatile reagents was removed under reduced pressure and, after addition of salted water, the solution was extracted with ethyl acetate. The extracts were washed with salted water and then with water, dried and evaporated to give a mixture of three compounds having Rf 0.35, 0.42, and 0.53 respectively in the solvent system toluene:ethyl acetate (1:1 by volume). The major compound, that having the lowest Rf value, was isolated by preparative TLC thereby obtaining 125 mg of the title compound in pure form.

EXAMPLE 9

6,3',2",5",3'",4'"-Hexa-O-acetyl-6'-O-benzoyl-4'-deoxy-penta-N-benzyloxycarbonylparomomycin (6; A=acetyl)

To a refluxing solution of 125 mg of the compound prepared in Example 8 in 8 ml of dry toluene under nitrogen atmosphere were added 0.4 ml of tributyltin hydride in 0.8 ml of toluene and 10 mg of azobisisobutyronitrile. After refluxing for 2½ hours, the reaction mixture was processed as described in Example 5 to give 70 mg of a product indistinguishable from the product of Example 5.

EXAMPLE 10

6,3',2",5",3'",4'"-Hexa-O-acetyl-6'-O-benzoyl-4'-O-[(phenylthio)thiocarbonyl]-penta-N-benzyloxycarbonylparomomycin (10; A=acetyl)

A solution of the compound prepared in Example 3 (1 g) in 20 ml of dry pyridine was cooled to 0° and 4 g of (phenylthio)thiocarbonyl chloride and 100 mg of 4-dimethylaminopyridine were added. The mixture was stirred at room temperature for 5 days. Water and ice were added and the mixture extracted with chloroform. The extracts were washed with water, 2 N hydrochloric acid, water, sodium bicarbonate solution, and water, in that order, and dried and evaporated. The residue was chromatographed on silica gel (toluene:ethyl acetate, 1:1 by volume) and a further purification was achieved by preparative TLC and reprecipitation from chloroform:ether:hexane to give 600 mg of the title compound, chromatographically homogeneous, having an Rf of 0.34 in the solvent system toluene:ethyl acetate (1:1 by volume).

EXAMPLE 11

6,3',2'',5'',3''',4'''-Hexa-O-acetyl-6'-O-benzoyl-4'-deoxy-penta-N-benzyloxycarbonylparomomycin (6; A=acetyl)

To a refluxing solution of the compound prepared in Example 10 (320 mg) in 13 ml of dry toluene, under nitrogen atmosphere, were added 2 ml of tributyltin hydride diluted with 4 ml of toluene and 30 mg of azobisisobutyronitrile. After refluxing for 2 hours, work-up as described in Example 5 gave 50 mg of the title compound.

EXAMPLE 12

4'-Deoxy-4'-epi-chloro-penta-N-benzyloxycarbonyl-paromomycin (11)

215 mg of the compound prepared in Example 4 were dissolved in 9 ml of 0.05 N methanolic sodium methoxide and stirred for 3 hours at room temperature. Work-up as described in Example 6 followed by preparative TLC gave 125 mg of the title compound in pure form, having an Rf of 0.33 in the eluant system chloroform:ethyl acetate:methanol (40:25:9 by volume).

EXAMPLE 13

4'-Deoxy-4'-epi-chloro-paromomycin (12)

125 mg of the compound prepared in Example 12 were dissolved in 16 ml of methanol, 6 ml of dioxan, 2.8 ml of water, and 1.4 ml of acetic acid. 205 mg of 10% palladium-on-carbon were added and the mixture was hydrogenated at room temperature and pressure for 5 hours. After 2 hours more catalyst (100 mg) was added. The reaction mixture was filtered, washed with ethyl acetate, concentrated and freeze-dried to give a residue that was purified on a column of CG 50 ($NH_4^+$ form, 100-200 mesh) affording 52 mg of the title compound in pure form, m.p. 160°-165° with decomposition.

The product was homogeneous on TLC in the solvent system 28% ammonia:butanol:ethanol:water (5:8:10:7 by volume) and had an Rf (double development) of 0.36.

Mass spectrum (field desorption) showed a peak at m/e 634 (MH+) and a peak m/e 598 (MH+-HCl).

What is claimed is:

1. A compound of the formula:

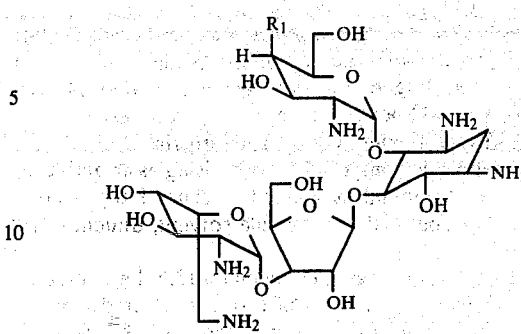

wherein $R_1$ represents a hydrogen or chlorine atom and pharmaceutically acceptable acid addition salts of said compound, said acid being selected from the group consisting of citric acid, ascorbic acid, acetic acid, hydrochloric acid, sulfuric acid, maleic acid, nitric acid, phosphoric acid and hydrobromic acid.

2. 4'-deoxy-paromomycin.

3. 4'-deoxy-4'-epi-chloro-paromomycin.

4. 4'-deoxy-4'-epi-chloro-penta-N-benzyloxycarbonylparomomycin.

5. 4'-deoxy-penta-N-benzyloxycarbonylparomomycin.

6. 6,3',2'',5'',3''',4'''-hexa-O-acetyl-6'-O-benzoyl-4'-deoxy-penta-N-benzyloxycarbonylparomomycin.

7. 6,3',2'',5'',3''', 4'''-hexa-O-acetyl-6'-O-benzoyl-4'-epi-chloro-4'-deoxy-penta-N-benzyloxycarbonyl-paromomycin.

8. 6,3',2'',5'',3''',4'''-hexa-O-acetyl-6'-O-benzoylpenta-N-benzyloxycarbonylparomomycin.

9. 6,3',2'',5'',3''',4'''-hexa-O-acetyl-6'-O-benzoyl-4'-O-[(methylthio)-thiocarbonyl]-penta-N-benxyloxycarbonylparomomycin.

10. 6,3',2'',5'',3''',4'''-hexa-O-acetyl-6'-O-benzoyl-4'-O-[(phenylthio)-thiocarbonyl]-penta-N-benzyloxycarbonylparomomycin.

11. A process for the preparation of a compound of the formula (I) as defined in claim 1, wherein $R_1$ represents a hydrogen atom, the process comprising converting the 6,3',2'',5'',3''', and 4''' hydroxy groups of 4',6'-O-benzylidene-penta-N-benzyloxycarbonylparomomycin to O-acyl or O-benzoyl groups by acylation or benzoylation, hydrolyzing the resultant hexa-O-acyl or benzoyl-4',6'-O-benzylidene-penta-N-benzylcarbonyl-paromomycin, converting the 6'-hydroxy group of the resultant 6,3'2'',5'',3''',4'''-hexa-O-acyl or benzoyl-penta-N-benzyloxycarbonylparomomycin to a 6'-O-benzoyl group by selective benzoylation, and chlorinating the resultant compound with sulphuryl chloride to obtain the 4'-deoxy-4'-epichloroderivative which, by means of tributyltin hydride, is reduced to the 4'-deoxy derivative which, by hydrolysis and catalytic hydrogenation, gives 4'-deoxy-paromomycin.

12. A process for the preparation of a compound of the formula (I) as defined in claim 1, wherein $R_1$ represents a chlorine atom, the process comprising converting the 6,3',2'',5'',3''' and 4''' hydroxy groups of 4',6'-O-benzylidene-penta-N-benzyloxycarbonylparomomycin to O-acyl or O-benzoyl groups by acylation or benzoylation, hydrolyzing the resultant hexa-O-acyl or benzoyl-4',6'-O-benzylidene-penta-N-benzyloxycarbonyl-paromomycin, converting the 6'-hydroxy group of the resultant 6,3',2'',5'',3''',4'''-hexa-O-acyl or benzoyl-penta-N-benzyloxycarbonylparomomycin to a 6'-O-benzoyl group by selective benzoylation, chlorinating the resultant compound with sulphuryl chloride, deacylating or debenzoylating the resultant compound, and catalytically hydrogenating the resultant 4'-deoxy-4'-epi-chloro-penta-N-benzyloxycarbonylparomomycin to give 4'-deoxy-4'-epi-chloro-paromomycin.

13. An antibiotic composition comprising as an active ingredient a compound as defined in claim 1 together with a pharmaceutically acceptable solvent, diluent or carrier.

14. A composition as defined in claim 13, wherein the active ingredient in the form of a salt is selected from the group consisting of the citric acid, ascorbic acid, acetic acid, hydrochloric acid, sulfuric acid, maleic acid, nitric acid, phosphoric acid, and hydrobromic acid salts.

15. A method of treating ameobic dysentery in human beings and in animals, which method comprises administering an effective amount of a compound as defined in claim 1 to the human being or animal.

16. A process for the preparation of a compound of the formula (I) as defined in claim 1, wherein $R_1$ represents a hydrogen atom, the process comprising converting the 6,3',2",5",3''', and 4''' hydroxy groups of 4',6'-O-benzylidene-penta-N-benzyloxycarbonylparomomycin to O-acyl or O-benzoyl groups by acylation or benzoylation, hydrolyzing the resultant hexa-O-acyl or benzoyl-4',6'-O-benzylidene-penta-N-benzylcarbonyl-paromomycin, converging the 6'-hydroxy group of the resultant 6,3'2",5",3''',4'''-hexa-O-acyl or benzoyl-penta-N-benzyloxycarbonylparomomycin to a 6'-O-benzoyl group by selective benzoylation, and converting the resultant compound into the corresponding S-methyldithiocarbonate by treatment with carbon disulphide, a strong base, and methyl iodide, reducing the resultant 6,3',2",5",3''',4'''-hexa-O-acyl or benzoyl-6'-O-benzoyl-4'-O-[(methylthio)-thiocarbonyl]-penta-N-benzyloxycarbonylparomomycin with tributyltin hydride to obtain the 4'-deoxy derivative which, by hydrolysis and catalytic hydrogenation, gives 4'-deoxy-paromomycin.

17. A process for the preparation of a compound of the formula (I) as defined in claim 1, wherein $R_1$ represents a hydrogen atom, the process comprising converting the 6,3',2",5",3''', and 4''' hydroxy groups of 4',6'-O-benzylidene-penta-N-benzyloxycarbonylparomomycin to O-acyl or O-benzoyl groups by acylation or benzoylation, hydrolyzing the resultant hexa-O-acyl or benzoyl-4',6'-O-benzylidene-penta-N-benzylcarbonyl-paromomycin, converging the 6'-hydroxy group of the resultant 6,3'2",5",3''',4'''-hexa-O-acyl or benzoyl-penta-N-benzyloxycarbonylparomomycin to a 6'-O-benzoyl group by selective benzoylation, and converting the resultant compound into the corresponding S-phenyldithiocarbonate by treatment with (phenylthio)-thiocarbonyl chloride in the presence of a base, reducing the resultant 6,3',2",5",3''',4'''-hexa-O-acyl or benzoyl-6'-O-benzoyl-4'-O[(phenylthio)thiocarbonyl]-penta-N-benzyloxycarbonylparomomycin with tributyline hydride to obtain the 4'-deoxy derivative which, by hydrolysis and catalytic hydrogenation, gives 4'-deoxy-paromomycin.

* * * * *

UNITED STATES PATENT AND TRADEMARK OFFICE
CERTIFICATE OF CORRECTION

PATENT NO. : 4,337,248

DATED : June 29, 1982

INVENTOR(S) : BATTISTINI et al.

Page 1 of 2

It is certified that error appears in the above-identified patent and that said Letters Patent are hereby corrected as shown below:

Column 9, line 44, change "accceptable" to --acceptable--;
Column 14, line 36, change "-benxyloxycar-" to ---benzyloxycar---;
Column 15, line 30, change "converging" to --converting--;
Column 16, line 28, change "tributyline" to --tributyltin--.
Column 3 and Column 4, change as follows:

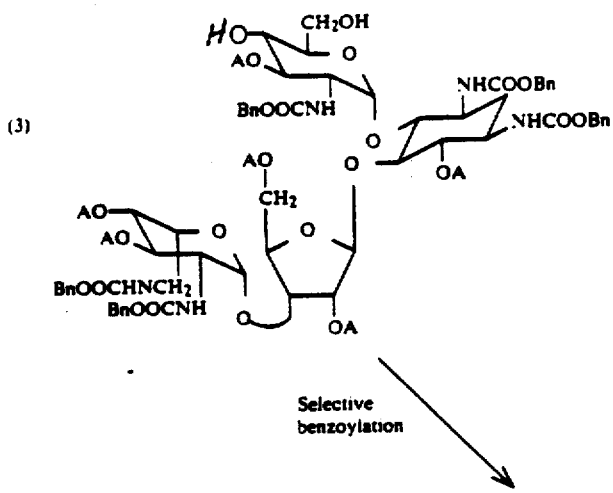

UNITED STATES PATENT AND TRADEMARK OFFICE
CERTIFICATE OF CORRECTION

PATENT NO. : 4,337,248

DATED : June 29, 1982

INVENTOR(S) : BATTISTINI et al.

It is certified that error appears in the above—identified patent and that said Letters Patent is hereby corrected as shown below:

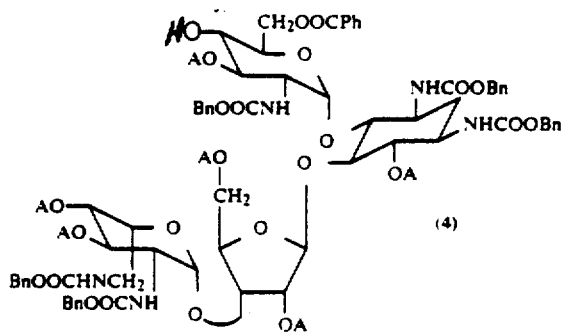

(4)

Signed and Sealed this

Fifteenth Day of February 1983

[SEAL]

Attest:

*Attesting Officer*

GERALD J. MOSSINGHOFF

*Commissioner of Patents and Trademarks*